United States Patent
Olek et al.

(10) Patent No.: US 7,756,643 B2
(45) Date of Patent: Jul. 13, 2010

(54) METHOD FOR DETERMINING THE BIOLOGICAL EFFECT AND/OR ACTIVITY OF AT LEAST ONE DRUG, CHEMICAL SUBSTANCES AND/OR PHARMACEUTICAL COMPOSITION BASED ON THEIR EFFECT ON THE METHYLATION STATUS OF DNA

(75) Inventors: Alexander Olek, Berlin (DE); Kurt Berlin, Stahnsdorf (DE)

(73) Assignee: Epigenomics AG, Berlin (DE)

( * ) Notice: Subject to any disclaimer, the term of this patent is extended or adjusted under 35 U.S.C. 154(b) by 114 days.

(21) Appl. No.: 10/087,898

(22) Filed: Mar. 1, 2002

(65) Prior Publication Data

US 2004/0029117 A1 Feb. 12, 2004

Related U.S. Application Data

(60) Provisional application No. 60/272,484, filed on Mar. 1, 2001.

(51) Int. Cl.
*G01N 33/48* (2006.01)
*G06G 7/48* (2006.01)
(52) U.S. Cl. .......................................... 702/19; 703/11
(58) Field of Classification Search .................. 424/9.1; 702/19
See application file for complete search history.

(56) References Cited

U.S. PATENT DOCUMENTS 3,558,768 A * 1/1971 Klippel et al. ............... 424/494
6,331,393 B1 * 12/2001 Laird et al. .................... 435/6

OTHER PUBLICATIONS

Lorincz et al. "Dynamic Analysis of proviral Induction and De Novo Methylation: Implications for a Histone Deacetylase-Independent, Methylation Density-Dependent Mechanism of Transcriptional Repression" Molecular and Cellular Biology, (2000) pp. 842-850.*

* cited by examiner

*Primary Examiner*—Eric S Dejong
(74) *Attorney, Agent, or Firm*—Ramin Amirsehhi

(57) ABSTRACT

This invention is related to methods, systems and computer program products for determining the biological effect and/or activity of drugs, chemical substances and/or pharmaceutical compositions using their effect on DNA-methylation as a marker for their biological effect(s). The invention is further related to the use of the inventive methods, systems and computer program products in obtaining new biologically active compounds which can be used as so-called "lead"-compounds for new and effective medicaments and treatment strategies of, in particular, human diseases.

5 Claims, No Drawings

METHOD FOR DETERMINING THE BIOLOGICAL EFFECT AND/OR ACTIVITY OF AT LEAST ONE DRUG, CHEMICAL SUBSTANCES AND/OR PHARMACEUTICAL COMPOSITION BASED ON THEIR EFFECT ON THE METHYLATION STATUS OF DNA

CROSS-REFERENCE TO RELATED APPLICATIONS

The present application claims the benefit under 35 U.S.C. 119(e) of U.S. Provisional Patent Application Ser. No. 60/272,484, filed Mar. 1, 2001, the disclosure of which is incorporated herein by reference.

FIELD OF THE INVENTION

This invention is related to methods, systems and computer program products for determining the biological effect and/or activity of drugs, chemical substances and/or pharmaceutical compositions using their effect on DNA-methylation as a marker for their biological effect(s). The invention is further related to the use of the inventive methods, systems and computer program products in obtaining new biologically active compounds which can be used as so-called "lead"-compounds for new and effective medicaments and treatment strategies of, in particular, human, diseases.

BACKGROUND OF THE INVENTION

1. The Constant Need for New Compounds and Biologically Active Compounds for the Development of New Pharmaceutics and Medicaments The advance in medical research constantly leads to the discovery of yet unknown and complex diseases, for which new, specific and effective pharmaceuticals and treatments have to be developed. In a majority of such new cases, nothing is known about biological compounds which would/could be effective in treating such diseases.

In general, time plays an important role in these cases, since in most of the cases an effective drug/treatment has to be found very rapidly.

Furthermore, such developments currently involve very cost-intensive screening procedures until a particularly suited compound (often called "lead"-compound) is found which could then serve as a chemical basis for an effective treatment.

Another current development in the treatment of diseases is the so-called "personalized" treatment, in which an individually treatment schedule and/or pharmaceutical composition is applied to the individual patient. Since the treatment is directed or applied to a very limited scope and number of patients (i.e. only one patient) and diseases, such treatment again is very cost-intensive and therefore can only seldom be applied in an efficient manner.

Furthermore, problems arise with already known biological compounds in such a way that a) unwanted side effects are discovered, that limit the use of established pharmaceutics, and b) resistance can be found/are developed against major therapeutics (like in the case of antibiotic resistances) which limit the success of presently applied compounds.

In view of the above, there exists a constant need for new potential candidate compounds for the treatment of emerging new diseases, personalised medicine and, of course, alternative treatments for already known diseases. Furthermore, the need exists for a reliable, cost-effective, fast and automateable method for screening such new effective compounds.

2. Screening for New Biologically Active Compounds Using "Combinatorial Chemistry"

The method of combinatorial chemistry is described as a profound change in the strategies that biotechnology-based industries are deploying in the search for exploitable biology and to discover new products and develop new or improved processes. (see, for example, Bull A T, et al. "Search and discovery strategies for biotechnology: the paradigm shift." Microbiol Mol Biol Rev 2000 September; 64(3):573-606)

In general, combinatorial chemistry involves screening of a specific (or a set of specific) compound with a vast number of potential biological candidate substances (for example, proteins) that might interact with the compound. Interacting partners are selected and used for further screening. Initially screened and isolated compounds can be used as "lead"-compounds for the development of biologically active compounds useful for treatment of diseases.

Other methods and devices for combinatorial chemistry are described in, for example, U.S. Pat. No. 6,175,816 (Flavin, et al.; "Use of automated technology in chemical process research and development") U.S. Pat. No. 6,045,755 (Lebl, et al.; "Apparatus and method for combinatorial chemistry synthesis") U.S. Pat. No. 5,880,972 (Horlbeck; "Method and apparatus for generating and representing combinatorial chemistry libraries") and U.S. Pat. No. 5,721,099 (Still, et al.; "Complex combinatorial chemical libraries encoded with tags").

WO 00/71742 describes the "marriage" of solid-state electronics and neuronal function to create a new high-throughput electrophysiological assay to determine a compound's acute and chronic effect on cellular function. Electronics, surface chemistry, biotechnology, and fundamental neuroscience are integrated to provide an assay where the reporter element is an array of electrically active cells. This innovative technology was applied to neurotoxicity, and to screening compounds from combinatorial chemistry, gene function analysis, and basic neuroscience applications. Further disclosed are algorithms to analyze the action potential peak shape differences to indicate the pathway(s) affected by the presence of a new drug or compound; from that, aspects of its function in that cell are deduced. This observation is said to be exploited to determine the functional category of biochemical action of an unknown compound.

WO 00/23458 describes templated combinatorial chemical libraries comprised of a plurality of bifunctional molecules having both a chemical compound and a nucleic acid tag that defines the structure of the chemical compound and directs its synthesis.

Logani S, et al. ("Actions of Ginkgo Biloba related to potential utility for the treatment of conditions involving cerebral hypoxia." Life Sci 2000 Aug. 11; 67(12):1389-96) describe the use of HTS (high-throughput screening) libraries for reevaluation of the pharmacologic properties of substances such as extract from the leaves of *Ginkgo biloba* Linne (form. *Salisburia adiantifolia* Sm.).

Although the method of combinatorial chemistry exhibits several advantages in comparison to conventional methods for screening for biologically effective compounds which are useful for the development of new medicaments, there are still several drawbacks associated with this method.

The screening of a combinatorial chemistry library involves a screening for a multitude of different possible reactions and/or interactions of the compounds to be analysed with the interacting partners. Therefore, the reaction conditions are assumed crucial for the result of the screening. In particular, a compound which shows an interaction with a target in such a combinatorial assay in vitro might exhibit completely different reaction conditions in vivo which makes prediction of an effective compound very difficult and unreliable. As a result, an interaction in an in vitro combinatorial chemistry screening assay can always only give a hint for a potential biological function of the screened compound in vivo.

As a result, combinatorial chemistry screening involves a necessary second step; once a potential target/lead compound has been identified/found, the biological effect still has to be confirmed/determined in an in vivo context. This makes compound identification using this method unpredictable, slow and costly.

3. Methylation Pattern and Diseases 3.1 State of the Art in Methylation Analysis The modification of the genomic base cytosine to 5'-methylcytosine represents the epigenetic parameter which to date is the most important one and has been best examined. Nevertheless, methods exist today to determine comprehensive genotypes of cells and individuals, but no comparable methods exist to date to generate and evaluate epigenotypic information on a large scale.

In principle, there are three methods that differ in principle for determining the 5-methyl state of a cytosine in the sequence context.

The first method is based in principle on the use of restriction endonucleases (RE), which are methylation-sensitive". REs are characterized in that they produce a cut in the DNA at a certain DNA sequence which is usually 4-8 bases long. The position of such cuts can be detected by gel electrophoresis, transfer to a membrane and hybridization. Methylation-sensitive means that certain bases within the recognition sequence must be unmethylated for the step to occur. The band pattern after a restriction cut and gel electrophoresis thus changes depending on the methylation pattern of the DNA. However, most CpG that can be methylated are outside of the recognition sequences of REs, and thus cannot be examined.

The sensitivity of this method is extremely low (Bird, A. P., Southern, E. M., J. Mol. Biol. 118, 27-47). A variant combines PCR with this method; an amplification by two primers located on both sides of the recognition sequence occurs after a cut only if the recognition sequence is in the methylated form. In this case, the sensitivity theoretically increases to a single molecule of the target sequence; however, only individual positions can be examined, at great cost (Shemer, R. et al., PNAS 93, 6371-6376).

The second variant is based on the partial chemical cleavage of whole DNA, using the model of a Maxam-Gilbert sequencing reaction, ligation of adaptors to the ends thus generated, amplification with generic primers, and separation by gel electrophoresis. Using this method, defined regions having a size of less than thousands of base pairs can be examined. However, the method is so complicated and unreliable that it is practically no longer used (Ward, C, et al., J. Biol. Chem. 265, 3030-3033).

A new method for the examination of DNA to determine the presence of 5-methylcytosine is based on the specific reaction of bisulfite with cytosine. The latter is converted under appropriate conditions into uracil, which, as far as base pairing is concerned, is equivalent to thymidine, and which also corresponds to another base. 5-Methylcytosine is not modified. As a result, the original DNA is converted in such a manner that methylcytosine, which originally could not be distinguished from cytosine by its hybridisation behaviour, now can be detected by "normal" molecular biological techniques. All of these techniques are based on base pairing, which can now be completely exploited. The state of the art, as far as sensitivity is concerned, is defined by a method which includes the DNA to be examined in an agarose matrix, intended to prevent the diffusion and renaturing of the DNA (bisulfite reacts only with single-stranded DNA) and to replace all precipitation and purification steps by rapid dialysis (Olek, A., et al., Nucl. Acids. Res. 24, 5064-5066). Using this method, individual cells can be examined, which illustrates the potential of the method. However, so far only individual regions up to approximately 3000 base pairs in length have been examined, and an overall examination of cells to identify thousands of possible methylation events is not possible. However, this method is not capable of reliably analyzing minute fragments from small sample quantities. In spite of protection against diffusion, such samples are lost through the matrix.

3.2 State of the Art in the Use of the Bisulfite Technique

To date, barring few exceptions, (for example, Zeschnigk, M. et al., Eur. J. Hum. Gen. 5, 94-98; Kubota, T. et al., Nat. Genet. 16, 16-17), the bisulfite technique is only used in research. However, short specific pieces of a known gene after bisulfite treatment are routinely amplified and either completely sequenced (Olek, A. and Walter, J., Nat. Genet. 17, 275-276) or the presence of individual cytosine positions is detected by a "primer extension reaction" (Gonzalgo, M. L. and Jones, P. A., Nucl. Acids. Res. 25, 2529-2531), or enzyme cut (Xiong, Z. and Laird, P. W., Nucl. Acids. Res. 25, 2532-2534). All these references are from the year 1997. The concept of using complex methylation patterns for correlation with phenotypic data pertaining to complex genetic diseases, much less via an evaluation algorithm such as, for example, a neural network, has, so far, gone unmentioned in the literature; moreover, it cannot be performed according to the methodologies of the state of the art.

3.3 State of the Art with Respect to Methylation and the Diagnosis of Human Diseases In the past, modification of the methylation pattern was analysed in order to study and understand the genetic mechanisms which are involved in the outbreak or the progression of a disease. All this research was done in a piece-by-piece fashion by studying only one gene/chromosomal region at a time and no diagnosis/therapeutic treatment regimen was based on the methylation pattern modifications. In fact, the type of disease associated with the modification of the methylation pattern was known before methylation analysis was performed. Therefore, the following publications only indicate the wide-spread connection between modifications of the methylation patterns and human diseases. Modifications can include both hyper- or hypomethylation of selected sites of the DNA.

Disease associated with a modification of the methylation patterns are, for example:

Leukemia (Aoki E et al. "Methylation status of the p15INK4B gene in hematopoietic progenitors and peripheral blood cells in myelodysplastic syndromes" Leukemia 2000 April; 14(4):586-93; Nosaka K et al. "Increasing methylation of the CDKN2A gene is associated with the progression of adult T-cell leukemia" Cancer Res 2000 Feb. 15; 60(4):1043-8; Asimakopoulos F A et al. "ABL1 methylation is a distinct molecular event associated with clonal evolution of chronic myeloid leukemia" Blood 1999 Oct. 1; 94(7):2452-60; Fajkusova L. et al. "Detailed Mapping of Methylcytosine Positions at the CpG Island Surrounding the Pa Promoter at the bcr-abl Locus in CML Patients and in Two Cell Lines, K562 and BV173" Blood Cells Mol Dis 2000 June; 26(3):193-204; Litz C E et al. "Methylation status of the major break-point cluster region in Philadelphia chromosome negative leukemias" Leukemia 1992 January; 6(1):35-41)

Head and neck cancer (Sanchez-Cespedes M et al. "Gene promoter hypermethylation in tumors and serum of head and neck cancer patients" Cancer Res 2000 Feb. 15; 60(4):892-5)

Hodgkin's disease (Garcia J F et al. "Loss of p16 protein expression associated with methylation of the p16INK4A gene is a frequent finding in Hodgkin's disease" Lab Invest 1999 December; 79(12):1453-9)

Gastric cancer (Yanagisawa Y et al. "Methylation of the hMLH1 promoter in familial gastric cancer with microsatellite instability" Int J Cancer 2000 Jan. 1; 85(1):50-3)

Prostate cancer (Rennie P S et al. "Epigenetic mechanisms for progression of prostate cancer" Cancer Metastasis Rev 1998-99;17(4):401-9)

Renal cancer (Clifford S C et al. "Inactivation of the von Hippel-Lindau (VHL) tumor suppressor gene and allelic losses at chromosome arm 3p in primary renal cell carcinoma: evidence for a VHL-independent pathway in clear cell renal tumourigenesis" Genes Chromosomes Cancer 1998 July; 22(3):200-9)

Bladder cancer (Sardi I et al. "Molecular genetic alterations of c-myc oncogene in superficial and locally advanced bladder cancer" Eur Urol 1998;33(4):424-30)

Breast cancer (Mancini D N et al. "CpG methylation within the 5' regulatory region of the BRCA1 gene is tumor specific and includes a putative CREB binding site" Oncogene 1998 Mar. 5; 16(9):1161-9; Zrihan-Licht S et al. "DNA methylation status of the MUC1 gene coding for a breast-cancer-associated protein" Int J Cancer 1995 Jul. 28; 62(3):245-51; Kass D H et al. "Examination of DNA methylation of chromosomal hot spots associated with breast cancer" Anticancer Res 1993 September-October; 13(5A):1245-51)

Burkitt's lymphoma (Tao Q et al. "Epstein-Barr virus (EBV) in endemic Burkitt's lymphoma: molecular analysis of primary tumor tissue" Blood 1998 Feb. 15; 91(4):1373-81)

Wilms tumor (Kleymenova E V et al. "Identification of a tumor-specific methylation site in the Wilms tumor suppressor gene" Oncogene 1998 Feb. 12; 16(6):713-20)

Prader-Willi/Angelman syndrome (Zeschnigh et al. "Imprinted segments in the human genome: different DNA methylation patterns in the Prader-Willi/Angelman syndrome region as determined by the genomic sequencing method" Human Mol. Genetics (1997) (6)3 pp 387-395; Fang P et al. "The spectrum of mutations in UBE3A causing Angelman syndrome" Hum Mol Genet 1999 January; 8(1):129-35)

ICF syndrome (Tuck-Muller et al. "CMDNA hypomethylation and unusual chromosome instability in cell lines from ICF syndrome patients" Cytogenet Cell Genet 2000;89(1-2):121-8)

Dermatofibroma (Chen T C et al. "Dermatofibroma is a clonal proliferative disease" J Cutan Pathol 2000 January; 27(1):36-9)

Hypertension (Lee S D et al. "Monoclonal endothelial cell proliferation is present in primary but not secondary pulmonary hypertension" J Clin Invest 1998 Mar. 1; 101(5):927-34)

Pediatric Neurobiology (Campos-Castello J et al. "The phenomenon of genomic "imprinting" and its implications in clinical neuropediatrics" Rev Neurol 1999 Jan. 1-15; 28(1):69-73)

Autism (Klauck S M et al. "Molecular genetic analysis of the FMR-1 gene in a large collection of autistic patients" Hum Genet 1997 August; 100(2):224-9)

Ulcerative colitis (Gloria L et al. "DNA hypomethylation and proliferative activity are increased in the rectal mucosa of patients with long-standing ulcerative colitis" Cancer 1996 Dec. 1; 78(11):2300-6)

Fragile X syndrome (Hornstra I K et al. "High resolution methylation analysis of the FMR1 gene trinucleotide repeat region in fragile X syndrome" Hum Mol Genet 1993 October; 2(10):1659-65)

Huntington's disease (Ferluga J et al. "Possible organ and age-related epigenetic factors in Huntington's disease and colorectal carcinoma" Med Hypotheses 1989 May; 29(1):51-4)

All the above-cited documents are hereby incorporated by reference.

Furthermore, it is known that the methylation pattern of methylation sensitive sites of other genes that are associated with other diseases is modified during the acute or non-acute phases of these diseases. Those genes are depicted in the listing of genes that is enclosed in this application and are associated with, for example, diseases related to angiogenesis, apoptosis, behavior, disorders of the cell cycle, cell signalling, developmental disorders, diseases related with DNA adducts, DNA damage, disorders in DNA replication, gene regulation, diseases related to immunological disorders, disturbances of the metabolism, metastasis, diseases related to miscellaneous clinical syndromes, pharmacological conditions, diseases related to a disturbed signal transduction, disturbed transcription, and tumour suppression/oncogene related diseases.

SUMMARY OF THE INVENTION

In view of the foregoing, an object of the invention is to provide methods, systems and computer program products for determining the biological effect and/or activity of drugs, chemical substances and/or pharmaceutical compositions using their effect on DNA-methylation as a marker for their biological effect(s).

A further object of the invention is to provide the inventive systems, methods and computer program products for their use in determining a drug, chemical substance and/or pharmaceutical composition that is biologically effective and/or active.

A further object of the invention is to provide biologically effective and/or active drugs, chemical substances and/or pharmaceutical compositions, which can be obtained using a method according to the invention.

A further object of the invention is to provide the biologically effective and/or active drug, chemical substance and/or pharmaceutical composition which is obtained using a method according to the invention for the use in a treatment of a disease and/or medical condition.

A further object of the invention is to provide systems, methods and computer program products for performing any of the inventive methods.

A further object of the invention is to provide a treatment of a disease and/or medical condition, based on a biologically effective and/or active drug, chemical substance and/or pharmaceutical composition according to the invention.

This object is solved according to the present invention by providing a method for determining the biological effect and/or activity of at least one drug, chemical substance and/or pharmaceutical composition, which comprises the steps of:

(a) obtaining a biological sample A containing DNA from at least one individual, tissue, cell or other biological material containing DNA, which was exposed to said at least one drug, chemical substance and/or pharmaceutical composition;

(b) obtaining a biological sample B containing DNA from at least one individual, tissue, cell or other biological material containing DNA, which was not exposed to said at least one drug, chemical substance or pharmaceutical composition;

(c) analysing the level of cytosine methylation at chosen sites of the DNA contained in the samples A and B;

(d) selecting the sites which are differentially methylated between the DNA in samples A and B, whereby a knowledge base is generated; and (e) concluding from the said knowledge base on the biological effect and/or activity of said at least one drug, chemical substance or pharmaceutical composition.

The present invention uses the modifications in the methylation pattern of the DNA for screening of biologically effective substances. In general, the invention uses the fact that the biological effect of a potentially biologically effective drug, chemical substance or pharmaceutical composition results in a modification of the DNA-methylation pattern of a cell or biological test system upon contact with the drug, chemical substance or pharmaceutical composition. Analysis of the modification of the pattern allows a direct conclusion about the biological effect of the drug, chemical substance or pharmaceutical composition in vivo and its potential application in the treatment of diseases or medical conditions.

The invention has several advantages in comparison to other screening methods, in particular combinatorial chemistry. First, the reaction conditions of the drug, chemical substance or pharmaceutical composition with the biological test system can be controlled in a very reliable manner. Modifications can be applied in a highly reproducible way due to the simplicity of the assay procedure and conditions.

Second, the analysis of the methylation pattern of the DNA allows screening of the in vivo effect of the substance in a one-step procedure using one controllable reaction (namely, the bisulfite treatment in order to look at the methylation status) instead of millions of unknown interactions between drugs, chemical substances or pharmaceutical compositions compounds and compounds of the cell or biological test system.

Thirdly, screening for potential lead-compounds becomes less time consuming and less costly, since the complete screening and analysis procedure can be automated.

Fourth, the inventive method allows the inclusion of personal data into the selection/analysis procedure which allows for a personalised screening of drugs, chemical substances or pharmaceutical compositions.

Other preferred embodiments of the invention will become apparent to the person skilled in the art after reading the features of the dependent claims.

In one embodiment of the method according to the invention, the biological sample is obtained by means of a biopsy, by means of an operation on an individual, by means of a dissection, derived from a preserved biological sample, collected from body fluid(s) and/or collected directly from the environment. In general, the only prerequisite for such a biological sample is to contain DNA which can be used directly or indirectly for the methylation analysis.

In another embodiment of the method according to the invention, the biological sample comprises a eucaryotic and/or procaryotic cell line, a biopsy sample, blood, sputum, faeces, urine, cerebral liquid, tissue embedded in paraffin, tissue derived from eyes, intestine, brain, heart, prostata, kidney, lung, breast or liver, histological samples or a combination thereof.

A preferred method according to the invention is characterised in that the biological sample is obtained from biological material of healthy and/or diseased individuals. Such diseases include all diseases and/or medical conditions which involve a modification of the DNA methylation of the cell and include, for example, unwanted side effects of medicaments, cancers, metastasis, dysfunctions, damages or diseases of the central nervous system (CNS), aggressive symptoms or behavioural disorders, clinical, psychological and social consequences of brain injuries, psychotic disorders and disorders of the personality, dementia and/or associates syndromes, cardiovascular diseases, malfunctions or damages, diseases, malfunctions or damages of the gastrointestine, diseases, malfunctions or damages of the respiratory system, injury, inflammation, infection, immunity and/or reconvalescence, diseases, malfunctions or damages as consequences of modifications in the developmental process, diseases, malfunctions or damages of the skin, muscles, connective tissue or bones, endocrine or metabolic diseases, malfunctions or damages, headache, and sexual malfunctions or combinations thereof, leukemia, head and neck cancer, Hodgkin's disease, gastric cancer, prostate cancer, renal cancer, bladder cancer, breast cancer, Burkitt's lymphoma, Wilms tumor, Prader-Willi/Angelman syndrome, ICF syndrome, dermatofibroma, hypertension, pediatric neurobiological diseases, autism, ulcerative colitis, fragile X syndrome, and Huntington's disease.

In a further preferred method according to the invention, the biological samples A and B are obtained from the identical individual, tissue, cell or other biological material.

In a further preferred method according to the invention, the biological samples A and B are taken before, during and/or after onset of a treatment with said drug, chemical substance or pharmaceutical composition. This allows the use of the inventive method to monitor and/or modify an already employed treatment regimen and to screen for unwanted side effects of the initially employed drugs, chemical substances or pharmaceutical compositions which leads to a strictly "personalised" medicament and/or treatment.

An even more preferred method according to the invention further comprises the step of isolating DNA from the said samples before analysing the level of cytosine methylation at chosen sites in said isolated DNA. This facilitates the reliability and the handling of the DNA in the further analyses procedures. Nevertheless, the inventive method can be successfully be performed even without any purification of the DNA. The isolation of the DNA for performing the inventive method can be characterised in that the isolation of said DNA contained in said biological sample comprises isolating subcellular compartments, organelles, macromolecular structures and multiprotein complexes, partial or complete preparation of the DNA and/or partial digestion of the material with an enzyme selected from proteases, RNAses and/or DNAses or combinations thereof. The pre-isolation of only parts of the cells, like organelles or the like, allows a pre-selection of the genes to be analysed. Other methods mentioned above can limit the amount of cellular debris which could interfere with the further analysis.

In another embodiment of the method according to the invention, the analysis of the level of cytosine methylation comprises chemical treatment with bisulphite, hydrogen sulphite or disulphite, polymerase chain reaction (PCR), hybridisation analyses, sequencing, mass spectrometry and fluorescent, enzymatic, radioactive, dye and/or antibody labelling. In general, all methods for the analysis of the methylation statuses at selected sites of the DNA can be employed. Such methods are known to the skilled artisan and are described in, for example, Dahl et al., "Analysis of in vivo methylation." Methods Mol Biol 2000;130:47-57; Zhou Y. et al., "Use of a single sequencing termination reaction to distinguish between cytosine and 5-methylcytosine in bisulfite-modified DNA." Biotechniques 1997 May; 22(5):850-4; Yoder J A et al. "Genetic analysis of genomic methylation patterns in plants and mammals." C Biol Chem 1996 October; 377(10):605-10 and others.

Another preferred method according to the invention is characterised in that all potentially methylated sites of the DNA are analysed. Such sites usually include all so-called "CpG"-islands on a given DNA sequence and are readily detectable by the person skilled in the art. Preferably, the level of at least two cytosine methylation sites is analysed in parallel, in order to test the potential effect of the drug, chemical substance or pharmaceutical composition on more than one methylation site. Preferably, the level of at least 100 cytosine methylation sites is analysed in parallel. The analysis of a multitude of sites in parallel allows for both an effective screening and a statistically highly relevant result of the method.

In general, the effect of the drug, chemical substance or pharmaceutical composition to be analysed on the biological cell, tissue or other biological system results in a modification of the expression of the genes of the respective cell, tissue or other biological system. Nevertheless, it is further preferred to analyse methylation sites that are located in methylation relevant regions of the DNA other than the genes themselves and which comprise complete genes and/or promoters, introns, first exons and/or enhancers. From the analysis of the methylation sites which are relevant for the expression of a certain gene, but not localised inside the sequence of the gene itself, the effect of the site for the expression of the gene can be readily extrapolated by the person skilled in the art.

For example, such methylation sites are located in methylation relevant regions of genes related with unwanted side effects of medicaments, cancers, metastasis, dysfunctions, damages or diseases of the central nerval system (CNS), aggressive symptoms or behavioural disorders, clinical, psychological and social consequences of brain injuries, psychotic disorders and disorders of the personality, dementia and/or associates syndromes, cardiovascular diseases, malfunctions or damages, diseases, malfunctions or damages of the gastrointestine, diseases, malfunctions or damages of the respiratory system, injury, inflammation, infection, immunity and/or reconvalescence, diseases, malfunctions or damages as consequences of modifications in the developmental process, diseases, malfunctions or damages of the skin, muscles, connective tissue or bones, endocrine or metabolic diseases, malfunctions or damages, headache, and sexual malfunctions or combinations thereof. Examples for genes, that are related to diseases related to angiogenesis, apoptosis, behavior, disorders of the cell cycle, cell signalling, developmental disorders, diseases related with DNA adducts, DNA damage, disorders in DNA replication, gene regulation, diseases related to immunological disorders, disturbances of the metabolism, metastasis, diseases related to miscellaneous clinical syndromes, medical and pharmacological conditions, diseases related to a disturbed signal transduction, disturbed transcription, and tumour suppression/oncogene related diseases are depicted in the listing enclose in this application. An effect of the drug, chemical substance or pharmaceutical composition to be analysed on the methylation statuses of sites which are relevant for the expression for gene(s) known to be related with these diseases would allow one to directly connect the tested drug, chemical substance or pharmaceutical composition with an effect on those genes and therefore allow the identification of possibly valuable new lead compounds as well as therapeutically important compounds.

Particularly preferred is a method according to the invention which is characterised in that the methylation sites are located in methylation relevant regions of genes related with leukemia, head and neck cancer, Hodgkin's disease, gastric cancer, prostate cancer, renal cancer, bladder cancer, breast cancer, Burkitt's lymphoma, Wilms tumor, Prader-Willi/Angelman syndrome, ICF syndrome, dermatofibroma, hypertension, pediatric neurobiological diseases, autism, ulcerative colitis, fragile X syndrome, and Huntington's disease.

For the use of the inventive method for personalised medicine, it is preferred that the analysed methylation sites are disease specific and/or personalised. This means, that a selection of sites is performed before the methylation analysis which allows a search which "looks" for an effect of a drug, chemical substance or pharmaceutical composition that is specifically suited (designed) for the individual need of the patient.

A further preferred method according to the invention is characterised in that the selection is based on the result of at least two individual rows of analyses. This will reduce the statistical error for the value of the methylation sensitivity of a selected site with an only limited increase of the costs for the analysis. In another preferred method according to the invention, the selection is performed in such a way to give a knowledge base comprising only one set of selected sites. Thus, the knowledge base will comprise only "on" and "off" type of data which allows for a very simple decision between different effects of different drugs, chemical substances or pharmaceutical compositions. In yet another embodiment of the inventive method, the selection is performed in such a way to result in a knowledge base comprising different classes of selected sites. Such classes can be referred to as "quality classes" which allows for a much more differentiated analysis of the effect of the drugs, chemical substances or pharmaceutical compositions to be analysed. The term "quality classes" as used herein comprises all different possibilities of grouping the different sites. Such groupings could, for example, include different importance for the selected sites for the analysis of the biological effect as well as statistical preciseness and/or quality of the analysis data of the selected site.

In a preferred method according to the invention, the selection is at least partially performed automatically by means of a suited automate, e.g. a computer device. Such device would be equipped with the necessary software for the analysis of the methylation sites and could be connected to an inter- or intranet, be part of a neural network or the like. The necessary data/information for the analyses can be present on the system directly or at a remote source, to which the device is directly or indirectly connected, for example via the internet.

In a preferred method according to the invention, at least two sites are selected in parallel. More preferably, at least 100 sites are selected in parallel. For the calculation of the results of the selection and the conclusion, all or only a part of the sites of the knowledge base can be used. In another embodiment of the method according to the invention, additional information about the biological sample is used for the conclusion. This additional information can comprise personal patient data, disease specific data, prior treatment data and/or additional methylation specific data.

According to another aspect of the method of the present invention, the conclusion is based on the result of at least two individual rows of analyses. This provides for an internal control run of the data which is used for the conclusion and increases the preciseness of the results. Preferably, the conclusion is performed by a computer system. Such device would be equipped with the necessary software for the conclusion and could be connected to an inter- or intranet, be part of a neural network or the like. The necessary data/information for the conclusion can be present on the system directly or at a remote source, to which the device is directly or indirectly connected, for example via the internet.

Another embodiment of the method according to the invention is characterised in that steps a) to d) are repeated. Repeating the method of the invention suits several different purposes. First, as mentioned above, the statistical quality of the of the resulting data increases. Second, an internal control can be provided, whether the biological sample was taken correctly and resembles e.g. the tissue of interest. Third, the inventive method can be repeated after a certain time after taking the first sample in order to provide for a monitoring of the effect of the drug(s), chemical substance(s) or pharmaceutical composition(s) to be analysed over time. This information could be included in the results of the analysis in order to provide a more precise picture of the biological effect of the drug, chemical substance or pharmaceutical composition to be analysed. With the commonly used method of combinatorial chemistry, this aspect can not be analysed since this method uses a "dead" system for the analysis of the compounds.

In one embodiment, the method of the invention is characterised in that the identical biological sample, different biological samples or a combination thereof is used in steps a) and/or b). In another embodiment the method of the invention is characterised in that steps c) to d) are repeated. The number of repeating "cycles" of the invention can vary depending on the individual case, e.g. depending on the quality of the sample to be analyse. One possibility would be to repeat the method of the invention for at least 5 to 50 times.

Preferably, such method according to the invention is characterised in that the method is at least partially performed by means of a suited automate, for example a robot and/or a computer system. The inventive method can be conveniently automated and/or computerized and respective devices and programs are readily known to the person skilled in the art.

A still further object of the invention is the use of the inventive method for determining at least one drug, chemical substance and/or pharmaceutical composition that is biologically effective and/or active.

Preferred is a use, wherein said at least one drug, chemical substance and/or pharmaceutical composition is biologically effective and/or active in the treatment of unwanted side effects of medicaments, cancers, metastasis, dysfunctions, damages or diseases of the central nerval system (CNS), aggressive symptoms or behavioural disorders, clinical, psychological and social consequences of brain injuries, psychotic disorders and disorders of the personality, dementia and/or associates syndromes, cardiovascular diseases, malfunctions or damages, diseases, malfunctions or damages of the gastrointestine, diseases, malfunctions or damages of the respiratory system, injury, inflammation, infection, immunity and/or reconvalescence, diseases, malfunctions or damages as consequences of modifications in the developmental process, diseases, malfunctions or damages of the skin, muscles, connective tissue or bones, endocrine or metabolic diseases, malfunctions or damages, headache, and sexual malfunctions or combinations thereof.

Even more preferred is a use, wherein said at least one drug, chemical substance and/or pharmaceutical composition is biologically effective and/or active in the treatment of leukemia, head and neck cancer, Hodgkin's disease, gastric cancer, prostate cancer, renal cancer, bladder cancer, breast cancer, Burkitt's lymphoma, Wilms tumor, Prader-Willi/Angelman syndrome, ICF syndrome, dermatofibroma, hypertension, pediatric neurobiological diseases, autism, ulcerative colitis, fragile X syndrome, and Huntington's disease.

Another aspect of the invention is a biologically effective and/or active drug, chemical substance and/or pharmaceutical composition which is obtained according to a method according to the invention. Accordingly, another aspect of the invention is, to use such a biologically effective and/or active drug, chemical substance and/or pharmaceutical composition according for the treatment of a disease and/or medical condition.

Preferably, such disease and/or medical condition is related to unwanted side effects of medicaments, cancers, metastasis, dysfunctions, damages or diseases of the central nerval system (CNS), aggressive symptoms or behavioural disorders, clinical, psychological and social consequences of brain injuries, psychotic disorders and disorders of the personality, dementia and/or associates syndromes, cardiovascular diseases, malfunctions or damages, diseases, malfunctions or damages of the gastrointestine, diseases, malfunctions or damages of the respiratory system, injury, inflammation, infection, immunity and/or reconvalescence, diseases, malfunctions or damages as consequences of modifications in the developmental process, diseases, malfunctions or damages of the skin, muscles, connective tissue or bones, endocrine or metabolic diseases, malfunctions or damages, headache, and sexual malfunctions or combinations thereof. Other diseases would be diseases related to angiogenesis, apoptosis, behavior, disorders of the cell cycle, cell signalling, developmental disorders, diseases related with DNA adducts, DNA damage, disorders in DNA replication, gene regulation, diseases related to immunological disorders, disturbances of the metabolism, metastasis, diseases related to miscellaneous clinical syndromes, medical and pharmacological conditions, diseases related to a disturbed signal transduction, disturbed transcription, and tumour suppression/oncogene related diseases.

Most preferably, said disease and/or medical condition is leukemia, head and neck cancer, Hodgkin's disease, gastric cancer, prostate cancer, renal cancer, bladder cancer, breast cancer, Burkitt's lymphoma, Wilms tumor, Prader-Willi/Angelman syndrome, ICF syndrome, dermatofibroma, hypertension, pediatric neurobiological diseases, autism, ulcerative colitis, fragile X syndrome, and/or Huntington's disease.

Another aspect of the invention is related to a method for the treatment of a disease and/or medical condition, which comprises: a) providing at least one biologically effective and/or active drug, chemical substance and/or pharmaceutical composition obtained according to the invention; and b) installing a treatment for the disease and/or medical condition comprising application of the at least one biologically effective and/or active drug, chemical substance and/or pharmaceutical composition to the patient in need. Preferred in this context is a method according to the invention wherein said specific treatment is a disease specific and/or personalised.

Such personalised treatment cannot reasonably be achieved with methods of treatment according to the state of the art as present.

Particularly preferred is the use of the inventive method for the treatment of unwanted side effects of medicaments, cancers, dysfunctions, damages or diseases of the central nerval system (CNS), aggressive symptoms or behavioural disorders, clinical, psychological and social consequences of brain injuries, psychotic disorders and disorders of the personality, dementia and/or associates syndromes, cardiovascular diseases, malfunctions or damages, diseases, malfunctions or damages of the gastrointestine, diseases, malfunctions or damages of the respiratory system, injury, inflammation, infection, immunity and/or reconvalescence, diseases, malfunctions or damages as consequences of modifications in the developmental process, diseases, malfunctions or damages of the skin, muscles, connective tissue or bones, endocrine or metabolic diseases, malfunctions or damages, headache, and sexual malfunctions or combinations thereof. Furthermore, the inventive method can be used for the treatment of diseases and/or conditions which are related to the genes as depicted in the listing of genes enclosed in this application, namely genes related to angiogenesis, apoptosis, behavior, disorders of the cell cycle, cell signalling, developmental disorders, diseases related with DNA adducts, DNA damage, disorders in DNA replication, gene regulation, diseases related to immunological disorders, disturbances of the metabolism, metastasis, diseases related to miscellaneous clinical syndromes, medical and pharmacological conditions, diseases related to a disturbed signal transduction, disturbed transcription, and tumour suppression/oncogene related diseases.

Even more preferred is the use of the method according to the invention for the treatment of leukemia, head and neck cancer, Hodgkin's disease, gastric cancer, prostate cancer, renal cancer, bladder cancer, breast cancer, Burkitt's lymphoma, Wilms tumor, Prader-Willi/Angelman syndrome, ICF syndrome, dermatofibroma, hypertension, pediatric neurobiological diseases, autism, ulcerative colitis, fragile X syndrome, and Huntington's disease.

The invention shall now be explained in more detail by the following examples without limiting the scope of the concept of the invention.

The invention shall now be explained in more detail by the following examples without limiting the scope of the concept of the invention.

EXAMPLES

Example 1

Determination of the Biological Effect of Tumour Necrosis Factor (TNF)

The colon cancer cell line HAT-29P218 was treated with 10 ng/ml TNF-alpha 1 and 9 ng/ml TGF-beta 1 for 10 days. The media was exchanged after each treatment of 48 h and followed by supplementation TGF-alpha 1 and TGF-beta 1 at the indicated concentrations.

After 10 days, the cells of the cytokine treated and the untreated control cell line cultures were collected by centrifugation and the chromosomal DNA was prepared using QIAamp DNA Mini Kit as recommended by the manufacturer (Quiagen, Hilden, Germany).

Subsequently, the chromosomal DNAs were bisulphite treated as published, for example, according to Olek et al. (ref?**) 6 different multiplex PCR reactions were performed on the 3 bi-sulphite DNA samples (untreated control, TGF-alpha 1 and TGF-beta 1 treated samples) using Cy5-labelled primer. The products of the methylation specific PCR reactions performed on the same DNA samples were combined. These complex mixtures of 64 PCR products derived from the three DNA samples were comparatively hybridised onto oligo micro arrays representing 256 CpG and the methylation statuses of the CpGs were analysed (see, for example, WO 99/28498). Comparison of three individual hybridisation assays of 2 complex PCRs independently performed on the 3 samples showed that the methylation status of CpGs of the c-myc and the p16 genes were significantly changed by TNF-alpha 1 and TNF-beta 1, respectively.

Example 2

Screening of a Peptide Library

A peptide library was prepared in a 96-well culture plate which contained overlapping peptide fragments derived from the peptide sequence of human serum albumine (HSA). As positive controls, each of vasoactive intestinal peptide (VIP) and pituitary adenylate cyclase-activating polypeptide (PACAP) was added in one of the wells. Both peptides are known to protect T cells from activation-induced cell death through down-regulation of Fas ligand (FasL) (Delgado M et al. "Vasoactive Intestinal Peptide and Pituitary Adenylate Cyclase-Activating Polypeptide Inhibit Expression of Fas Ligand in Activated T Lymphocytes by Regulating c-Myc, NF-kappaB, NF-AT, and Early Growth Factors 2/3" J Immunol 2001 Jan. 15; 166(2):1028-1040).

A T-cell line (example?) was incubated together with the peptides and VIP or PACAP. After 10 days, the cells of the VIP/PACAP and HSA peptide treated as well as untreated control cell line cultures were collected by centrifugation and the chromosomal DNA was prepared using QIAamp DNA Mini Kit as recommended by the manufacturer (Quiagen, Hilden, Germany).

Subsequently, the chromosomal DNAs were bisulphite treated as published, for example, according to Olek et al. 6 different multiplex PCR reactions were performed on the 3 bisulphite DNA samples (untreated control, HSA and VIP/PACAP treated samples) using Cy5-labelled primer. The products of the methylation specific PCR reactions performed on the same DNA samples were combined. These complex mixtures of 64 PCR products derived from the three DNA samples were comparatively hybridised onto oligo micro arrays representing 256 CpG and the methylation statuses of the CpGs were analysed according to a method described in WO 99/28498. Comparison of three individual hybridisation assays of 2 complex PCRs independently performed on the 3 samples showed that the methylation status of CpGs of the Fas-L gene was significantly changed by VIP and PACAP, respectively whereas no changes were seen with HSA derived peptides.

Example 3

Screening of a Fractionated Plant Crude Extract

In order to analyse the anti-metastatic effect of Celosia argentea seed extracts (CAE), which have traditionally been used as a therapeutic drug for eye and hepatic diseases in China and Japan a water extract of the seeds was prepared. Hayakawa Y et al. ("Anti-metastatic and immunomodulating properties of the water extract from Celosia argentea seeds Biol Pharm Bull 1998 November; 21(11):1154-9") report that the anti-metastatic effect of CAE is based on its immunomodulating properties including induction of cytokines such as IL-12, IL-2 and IFN-gamma leading to a Th1 dominant immune state and activating macrophages to the tumoricidal state.

In order to prove this, macrophages were incubated with the CEA water extract which was added to culture media. After 10 days, the cells of the extract treated and the untreated control cell line cultures were collected by centrifugation and the chromosomal DNA was prepared using QIAamp DNA Mini Kit as recommended by the manufacturer (Quiagen, Hilden, Germany).

Subsequently, the chromosomal DNAs were bisulphite treated as published, for example, according to Olek et al. 6 different multiplex PCR reactions were performed on the 3 bisulphite DNA samples (untreated control and CEA treated samples) using Cy5-labelled primer. The products of the methylation specific PCR reactions performed on the same DNA samples were combined. These complex mixtures of 64 PCR products derived from the three DNA samples were comparatively hybridised onto oligo micro arrays representing 256 CpG and the methylation statuses of the CpGs were analysed (Olek et al. WO 99/28498). Comparison of three individual hybridisation assays of 2 complex PCRs independently performed on the 2 samples showed that the methylation status of CpGs of the IL-12, IL-2 and IFN-gamma genes were significantly changed by CEA water extract.

The invention claimed is:

1. A method for determining the biological effect and/or activity of at least one pharmaceutical composition, comprising the steps of:
   (a) obtaining a biological sample A containing DNA, said biological sample A being from at least one of an individual, a tissue, a cell or another biological material containing DNA, wherein said biological sample A was exposed to said at least one pharmaceutical composition, wherein said biological sample A is obtained from biological material of a diseased individual;
   (b) obtaining a biological sample B containing DNA, said biological sample B being from at least one of an individual, a tissue, a cell or another biological material containing DNA, wherein said biological sample B was not exposed to said at least one pharmaceutical composition, wherein said biological sample B is obtained from biological material of a diseased individual;
   (c) then, analyzing the level of cytosine methylation at chosen sites of the DNA contained in the biological samples A and B, characterized in that the level of at least 100 cytosine methylation sites is analyzed in parallel, wherein said analyzing step is performed using a suitably programmed computer;
   (d) selecting those of said chosen sites which are differentially methylated between the DNA in biological samples A and B, whereby a knowledge base is generated, wherein said selecting step is performed using a suitably programmed computer, and
   (e) concluding from said knowledge base a biological effect and/or activity that said at least one pharmaceutical composition has on said biological sample A in step (a) and communicating the conclusion to a computer via an internet or intranet connection, wherein said concluding step is performed using a suitably programmed computer.

2. A method for determining the biological effect and/or activity of at least one pharmaceutical composition, comprising the steps of:
   (a) obtaining a biological sample A containing DNA, said biological sample A being from at least one of an individual, a tissue, a cell or another biological material containing DNA, wherein said biological sample A was exposed to said at least one pharmaceutical composition, wherein said biological sample A is obtained from biological material of a diseased individual;
   (b) obtaining a biological sample B containing DNA, said biological sample B being from at least one of an individual, a tissue, a cell or another biological material containing DNA, wherein said biological sample B was not exposed to said at least one pharmaceutical composition, wherein said biological sample B is obtained from biological material of a diseased individual;
   (c) then, analyzing the level of cytosine methylation at chosen sites of the DNA contained in the biological samples A and B, wherein said analyzing step is performed using a suitably programmed computer;
   (d) selecting those of said chosen sites which are differentially methylated between the DNA in biological samples A and B, whereby a knowledge base is generated, characterized in that at least 100 sites are selected in parallel, wherein said selecting step is performed using a suitably programmed computer; and
   (e) concluding from said knowledge base a biological effect and/or activity that said at least one pharmaceutical composition has on said biological sample A in step (a) and communicating the conclusion to a computer via an internet or intranet connection, wherein said concluding step is performed using a suitably programmed computer.

3. A method for determining the biological effect and/or activity of at least one pharmaceutical composition, comprising the steps of:
   (a) obtaining a biological sample A containing DNA, said biological sample A being from at least one of an individual, a tissue, a cell or another biological material containing DNA, wherein said biological sample A was exposed to said at least one pharmaceutical composition, wherein said biological sample A is obtained from biological material of a diseased individual;
   (b) obtaining a biological sample B containing DNA, said biological sample B being from at least one of an individual, a tissue, a cell or another biological material containing DNA, wherein said biological sample B was not exposed to said at least one pharmaceutical composition, wherein said biological sample B is obtained from biological material of a diseased individual;
   (c) then, analyzing the level of cytosine methylation at chosen sites of the DNA contained in the biological samples A and B, wherein said analyzing step is performed using a suitably programmed computer;
   (d) selecting those of said chosen sites which are differentially methylated between the DNA in biological samples A and B, whereby a knowledge base is generated, wherein said selecting step is performed using a suitably programmed computer;
   (e) repeating steps a) to d); and
   (f) concluding from said knowledge base a biological effect and/or activity that said at least one pharmaceutical composition has on said biological sample A in step (a) and communicating the conclusion to a computer via an interne or intranet connection, wherein said concluding step is performed using a suitably programmed computer.

4. A method for determining the biological effect and/or activity of at least one pharmaceutical composition, comprising the steps of:

(a) obtaining a biological sample A containing DNA, said biological sample A being from at least one of an individual, a tissue, a cell or another biological material containing DNA, wherein said biological sample A was exposed to said at least one pharmaceutical composition, wherein said biological sample A is obtained from biological material of a diseased individual;

(b) obtaining a biological sample B containing DNA, said biological sample B being from at least one of an individual, a tissue, a cell or another biological material containing DNA, wherein said biological sample B was not exposed to said at least one pharmaceutical composition, wherein said biological sample B is obtained from biological material of a diseased individual;

(c) then, analyzing the level of cytosine methylation at chosen sites of the DNA contained in the biological samples A and B, wherein said analyzing step is performed using a suitably programmed computer;

(d) selecting those of said chosen sites which are differentially methylated between the DNA in biological samples A and B, whereby a knowledge base is generated, wherein said selecting step is performed using a suitably programmed computer, (e) repeating steps c) to d); and (f) concluding from said knowledge base a biological effect and/or activity that said at least one pharmaceutical composition has on said biological sample A in step (a) and communicating the conclusion to a computer via an internet or intranet connection, wherein said concluding step is performed using a suitably programmed computer.

5. A method for determining the biological effect and/or activity of at least one pharmaceutical composition, comprising the steps of:

(a) obtaining a biological sample A containing DNA, said biological sample A being from at least one of an individual, a tissue, a cell or another biological material containing DNA, wherein said biological sample A was exposed to said at least one pharmaceutical composition, wherein said biological sample A is obtained from biological material of a diseased individual;

(b) obtaining a biological sample B containing DNA, said biological sample B being from at least one of an individual, a tissue, a cell or another biological material containing DNA, wherein said biological sample B was not exposed to said at least one pharmaceutical composition, wherein said biological sample B is obtained from biological material of a diseased individual;

(c) then, analyzing the level of cytosine methylation at chosen sites of the DNA contained in the biological samples A and B, wherein said analyzing step is performed using a suitably programmed computer;

(d) selecting those of said chosen sites which are differentially methylated between the DNA in biological samples A and B, whereby a knowledge base is generated, wherein said selecting step is performed using a suitably programmed computer, and (e) concluding from said knowledge base a biological effect and/or activity that said at least one pharmaceutical composition has on said biological sample A in step (a) and communicating the conclusion to a computer via an internet or intranet connection, wherein said concluding step is performed using a suitably programmed computer, (f) wherein said method is repeated at least 5 to 50 times.

* * * * *